(12) United States Patent
Threlfall

(10) Patent No.: US 11,583,669 B2
(45) Date of Patent: Feb. 21, 2023

(54) PREPACKAGED NEEDLELESS INTRAVENOUS TUBING WITH IN-LINE DISINFECTANT PORT CAPS

(71) Applicant: Joan Kunec Threlfall, McLean, VA (US)

(72) Inventor: Joan Kunec Threlfall, McLean, VA (US)

(*) Notice: Subject to any disclaimer, the term of this patent is extended or adjusted under 35 U.S.C. 154(b) by 340 days.

(21) Appl. No.: 16/812,532

(22) Filed: Mar. 9, 2020

(65) Prior Publication Data
US 2020/0282198 A1    Sep. 10, 2020

Related U.S. Application Data

(60) Provisional application No. 62/815,744, filed on Mar. 8, 2019.

(51) Int. Cl.
| | |
|---|---|
| *A61M 39/16* | (2006.01) |
| *A61M 5/168* | (2006.01) |
| *A61M 39/18* | (2006.01) |
| *A61M 5/00* | (2006.01) |

(52) U.S. Cl.
CPC .......... *A61M 39/165* (2013.01); *A61M 5/002* (2013.01); *A61M 5/16804* (2013.01); *A61M 39/162* (2013.01); *A61M 39/18* (2013.01); *A61M 2209/06* (2013.01)

(58) Field of Classification Search
CPC .. A61M 39/165; A61M 5/002; A61M 39/162; A61M 39/18; A61M 2209/06; A61M 5/1414; A61M 39/20
See application file for complete search history.

(56) References Cited

U.S. PATENT DOCUMENTS

| | | | |
|---|---|---|---|
| 4,447,230 A | * | 5/1984 | Gula ................... A61M 5/1408 604/122 |
| 7,799,010 B2 | | 9/2010 | Tennican |
| 8,728,056 B2 | | 5/2014 | Colantonio et al. |
| 8,777,504 B2 | | 7/2014 | Shaw et al. |
| 9,072,868 B2 | | 7/2015 | Ziebol et al. |
| 9,399,125 B2 | | 7/2016 | Burkholz |
| 9,415,202 B2 | | 8/2016 | Solomon et al. |
| 9,440,062 B2 | | 9/2016 | Adams et al. |
| 9,527,660 B2 | | 12/2016 | Tennican |
| 9,533,136 B2 | | 1/2017 | Midgette et al. |

(Continued)

*Primary Examiner* — Bradley J Osinski
(74) *Attorney, Agent, or Firm* — Dunlap Bennett & Ludwig, PLLC; Anna L. Kinney

(57) ABSTRACT

A prepackaged needleless intravenous line assembly is provided as well as a method of delivering intravenous medication and/or fluid to a patient while maintaining sterility of needleless access ports. The pre-packaged needleless intravenous line assembly is a sterile intravenous line with at least one sterile access port, each access port having a disinfection cap installed thereon, sealed within a pouch with at least one strip of multiple sealed disinfection caps. An intravenous tubing kit, having sterile intravenous tubing with capped sterile access ports as well as sealed replacement disinfection caps, is removed from the package and attached to a patient's intravenous catheter. A disinfection cap is removed from the sterile access port. Medication and/or fluid is administered into the access port. A replacement disinfection cap is installed onto the access port.

12 Claims, 3 Drawing Sheets

(56) References Cited

U.S. PATENT DOCUMENTS

| | | |
|---|---|---|
| 2008/0177250 A1 | 7/2008 | Howlett et al. |
| 2009/0297400 A1 | 12/2009 | Cady et al. |
| 2015/0306369 A1* | 10/2015 | Burkholz .............. A61M 39/20 |
| | | 604/539 |
| 2016/0144118 A1 | 5/2016 | Solomon et al. |
| 2017/0095655 A1 | 4/2017 | Whitfield |
| 2017/0203087 A1 | 7/2017 | Ryan et al. |
| 2018/0021512 A1* | 1/2018 | Fukuoka ................ A61M 5/14 |
| | | 604/404 |
| 2018/0055962 A1 | 3/2018 | Drmanovic |
| 2018/0256883 A1 | 9/2018 | Follman et al. |

* cited by examiner

PREPACKAGED NEEDLELESS INTRAVENOUS TUBING WITH IN-LINE DISINFECTANT PORT CAPS

CROSS-REFERENCE TO RELATED APPLICATION

This application claims the benefit of priority of U.S. provisional application No. 62/815,744, filed Mar. 8, 2019, the contents of which are herein incorporated by reference.

BACKGROUND OF THE INVENTION

The present invention relates to medical aseptic techniques and devices and, more particularly, to a prepackaged needleless intravenous tubing with in-line disinfectant port caps.

Prepackaged needleless intravenous tubing is sterile until the package is opened. Once opened, the needleless ports are easily contaminated by hands, environment, syringe hubs, etc. Currently, there are no quick and easy to use systems for hands-on providers.

Patients are frequently given multiple, large doses of antibiotics at intervals during a surgical procedure "prophylactically". Approximately 150 million intravenous lines are placed yearly in the United States. Aseptic technique is fundamental to safe delivery of intravenous solutions and medications in the operating room and hospital. Concern for needle safety of health care workers has resulted in the creation of needle free products, but issues such as an increase in blood stream infections have resulted. Needleless connectors are a critical piece of equipment connecting to an intravenous line, enabling providers safe intravenous access. The needleless connector serves as a microbial GATE-KEEPER for vascular access. (See Curran, Evonne, Journal Infection Prevention, 2016 Sep. 17(5) 234-240. Consequently, how it is disinfected and if it is disinfected potentially determines how many organisms a patient is exposed to. Currently, health care worker compliance rate is as low as 10% according to studies. While colonization of needleless devices requires further study, there has been a 50% increase in post-insertion intravenous catheter-related infections since their introduction. According to the Centers for Disease Control and Prevention, the pooled mean inpatient ward rate for central line intravenous blood stream infections was 1.14 per 1000-line days and for peripheral intravenous lines, 0.5 per 1,000-line days. The cost per infection ranges from $6,000 to $29,000. Patients with bloodstream infections have a 12% to 25% chance of dying from the infection. Experts estimate 30,000 patients die yearly due to bloodstream infections. Proportionally, research is lacking in how many nosocomial infections are due to bloodstream infections. Nosocomial infections affect 10% of patients, amplifying the evolving problem of bacterial resistance to antibiotics.

Lack of compliance with disinfection of needleless ports, education, availability, and better disinfecting agents require randomized control studies to evaluate efficacy of practice. However, two practitioner habits are particularly noncompliant with evidence-based practices and place patients in danger of bloodstream infection: failure to properly disinfect ports and failure to cap ports. Needleless devices not being disinfected or capped allows opportunity for infection to be introduced. Although the optimal technique or disinfection time has not been identified, scrubbing needleless ports with alcohol for 5-60 seconds is recommended prior to use. Currently, no quick, efficient and effective method for needleless port access protection and disinfection exists, particularly if used where access to needleless ports is repeatedly required in seconds (such as the operating room and emergency room).

Passive disinfection caps, such as 3M™ CUROS™ devices, eliminate human factor issues requiring clinicians to carry separate disinfecting supplies or to remember to perform disinfection for the required time before accessing the port. Research data from 3M™ CUROS™ disinfectant caps indicate that these caps disinfect ports in one minute and protect ports for seven days, resulting in a 99.9% reduction in six types of bacteria associated with central line-associated bloodstream infections (CLABSI). Far more peripheral intravenous lines are placed than central lines, roughly 150 million peripheral lines compared to 3 million central lines, respectively. Many patients have more than one peripheral intravenous line with needleless ports. Medicine and other insurance carriers consider bloodstream infections preventable. Every patient with a needleless port intravenous line deserves optimal infection prevention consideration. One such disinfection cap is disclosed in published application number US 2018/0256883. However, the practitioner must still carry many disinfection caps from patient to patient to disinfect ports repeatedly between uses. Moreover, existing disinfection caps do not keep a port sterile as it emerges from its packaging.

Effective port hub disinfection is affected by the roughness or smoothness of the septum, the ability to clean the surface, and the grooves or gaps in the device seal. The greatest risk for microbial contamination of a patient's intravenous catheter after insertion is the needleless connector with 33%-45% contaminated and compliance with disinfection as low as 10%. Studies indicate a 48%-86% reduction in infections when passive alcohol disinfectant caps are used.

As can be seen, there is a need for a system that makes the needleless port disinfection process easy, practical, efficient and effective.

The present invention provides prepackaged intravenous lines with pre-capped access ports as well as attached replacement disinfection caps, which allows the hands-on provider immediate access to disinfection caps for intravenous access ports, thereby increasing compliance with evidence-based cleansing techniques. The purpose is to decrease nosocomial infections in patients with needleless port intravenous lines (whether with peripheral or central catheters).

In another embodiment, a connector, such as a clamp with a zip tie, with attached replacement disinfectant caps is provided. The connector may easily be added or replaced on any manufactured intravenous line.

SUMMARY OF THE INVENTION

As stated above, aseptic technique is fundamental to safe delivery of intravenous solutions and medications in the operating room. Any intravenous line can deliver life threatening bacteria. Currently, no quick and efficient system for port access which also allows access of ports multiple times exists. The invention claimed herein solves this problem and potentially greatly reduces the risks of infection. The claimed prepackaged intravenous line kit and associated method enables a safe process by ensuring intravenous ports are disinfected each time they are accessed. The claimed kit makes the needleless port disinfection process for hands-on providers easy, practical, efficient and effective.

In one aspect of the present invention, a prepackaged needleless intravenous line assembly is provided. The prepackaged assembly comprises a pouch within which a sterile intravenous line, having at least one sterile access port with a disinfection cap installed thereon, and a plurality of sealed disinfection caps are sealed. The plurality of sealed disinfection caps, passive and active, may be secured on a strip.

In another aspect of the present invention, a method of delivering intravenous medication and/or fluid to a patient while maintaining sterility of a needleless access port is provided. According to the method, a pre-packaged intravenous tubing kit having sterile intravenous tubing with one or more sterile access ports and a plurality of sealed replacement disinfection caps is provided, with each access port having a disinfection cap installed thereon. The intravenous tubing kit is removed from the package and the intravenous solution primed prior to attachment to the patient's intravenous catheter. The disinfection cap is removed from said sterile access port and fluid or medication is administered into said access port. One of the plurality of replacement disinfection caps is installed onto said access port.

In another aspect of the present invention, a replacement disinfection cap assembly is provided. The assembly comprises a connector that is removably connectable to intravenous tubing and at least one strip with a plurality of disinfection caps connected to the connector. The plurality of disinfection caps is selected from the group consisting of passive disinfection caps, active disinfection caps, and a combination thereof.

These and other features, aspects and advantages of the present invention will become better understood with reference to the following drawings, description and claims.

BRIEF DESCRIPTION OF THE DRAWINGS

FIG. 1A is a front view of the intravenous line assembly of FIG. 1, shown in a packaged position.

DETAILED DESCRIPTION OF THE INVENTION

Figure 1:
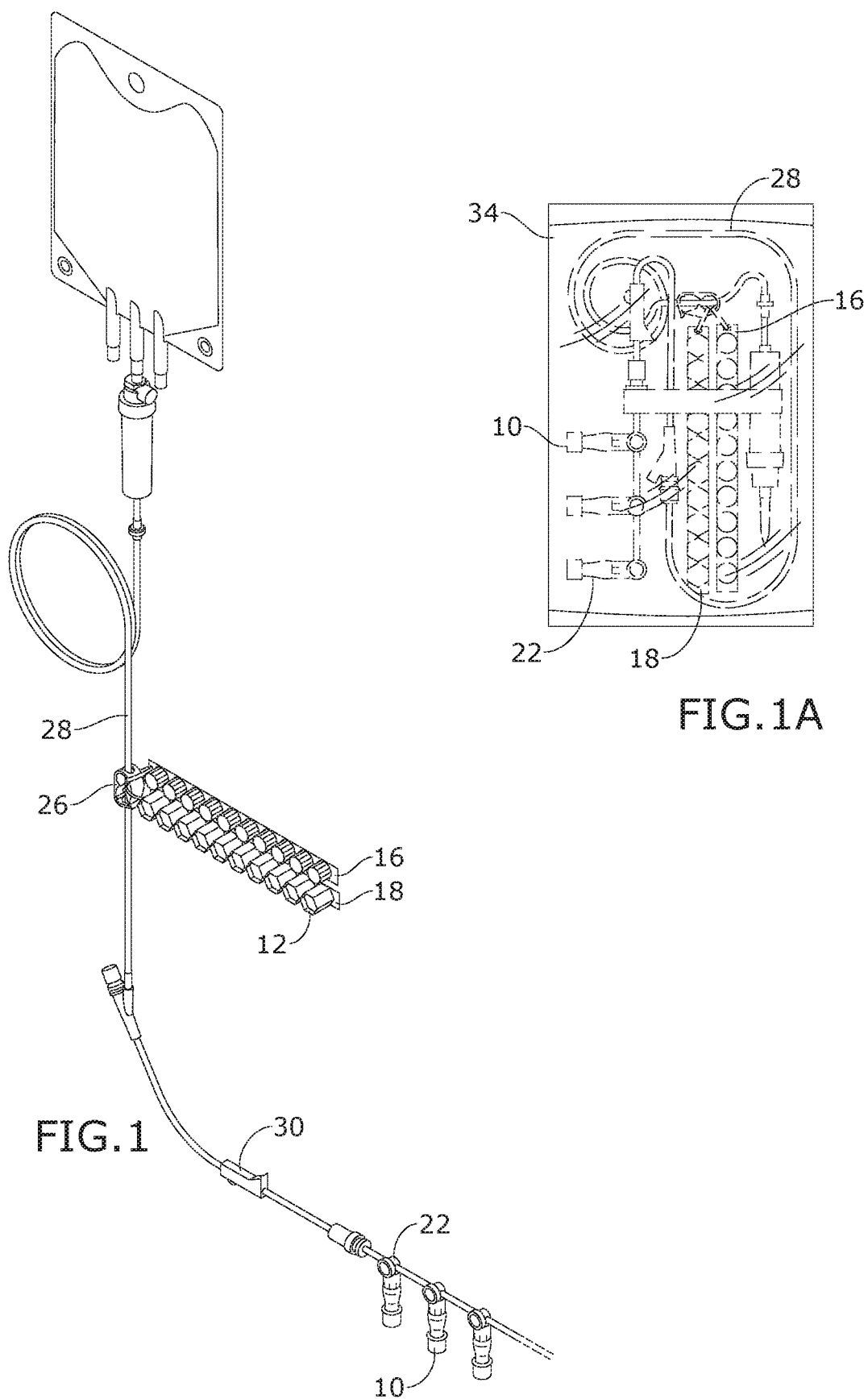
FIG. 1 is a schematic perspective view of an intravenous line assembly according to an embodiment of the invention, shown in use.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

As used herein, the term "strip" refers to a foil-backed dispenser with a plurality of disinfectant caps. The term "infusion connector" refers to a spike commonly provided on standard IV tubing.

A passive disinfection cap refers to port protector containing a disinfectant such as alcohol which is installed onto intravenous access points for disinfection and protection.

An active disinfection cap refers to a port protector that provides active mechanical friction to the disinfectant of the passive disinfection cap. Active disinfection caps have more disinfectant (i.e., are "wetter") than passive disinfection caps and have a textured "scrubbing" surface inside the cap. Active disinfectant caps disinfect ports much faster than passive disinfectant caps are therefore generally preferable when a provider expects to use a port again within a short period of time, e.g., seconds or minutes.

Broadly, one embodiment of the present invention is a prepackaged intravenous tubing system which allows quick and multiple access to intravenous ports in areas such as an operating room. Advantageously, the process of disinfecting ports is facilitated by using the claimed system.

The present invention includes standard needleless intravenous tubing and alcohol- or chlorhexidine-impregnated caps prepackaged together, so the hands-on provider has an immediately accessible product requiring no assembly. Additionally, attached replacement disinfectant port caps for needleless ports are ready to immediately replace a removed cap to protect needleless access and to prepare the port for use. The inventive kit provides a closed and aseptic system for needleless intravenous lines.

The inventive intravenous line kit may be packaged in any suitable packaging material that maintains the kit's sterility, such as a sealed polymeric pouch.

The prepackaged intravenous tubing with disinfectant port caps eliminates process issues relating to time and method, especially in the operating room environment, where intravenous lines are accessed quickly and multiple times. The inventive kit enables the provider to replace disinfection caps every time the needleless ports are utilized for fluid or drug administration to patients.

In another embodiment, the invention provides a clip-on replacement set of disinfectant caps comprising a connector, such as a clamp, connected to a strip of a plurality of passive disinfectant caps and a strip of active disinfectant caps. The inventive clip-on replacement set of disinfectant caps may be added to any intravenous line system.

The inventive method minimizes the exposure of the needleless ports to bacterial contamination. The needleless port remains sterile longer than previously available needleless intravenous lines because the needleless connector port remains capped until use. Moreover, the attached replacement caps reinforce compliance with the evidence-based procedure of cleaning ports between use. Replacement disinfection caps are readily available with the present invention; the provider does not have to search for supplies or carry bulky containers of supplies from patient to patient. Nor does the provider have to determine the amount of cleaning or disinfectant exposure time required to adequately disinfect the port.

According to an embodiment of the invention, a sterile needleless intravenous line system is prepackaged with fitted disinfection caps installed on each connector port. A strip of replacement passive disinfection caps, a strip of replacement active disinfection caps, or both are also provided within the sterile packaging. The replacement caps can be attached to the intravenous line device to protect ports between use and avoid potential swallowing of caps by infants and children. The caps may be attached to the needleless intravenous tubing system with any suitable connector, such as but not limited to a zip tie, a clamp, or a combination thereof.

According to an embodiment of the invention, a connector with attached strips of disinfectant caps may be added to any intravenous line system.

In one embodiment, fewer ports are preferable as they decrease contamination portals.

Beneficially, this system eliminates the need for clinicians to carry disinfecting supplies or remember to perform the required scrubbing process before accessing an intravenous line for medication and/or fluid administration to a patient. This process is particularly important in the operating room arena where multiple drugs are quickly being administered.

In another embodiment, the invention may be used in any environment where needleless intravenous line systems are used. For example, the system may be used in any veterinary surgical environment.

A method according to an embodiment of the invention implements the inventive kit. A provider may open the packaging to remove the prepackaged needleless intravenous (IV) line, insert an end of the intravenous line into the patient's intravenous catheter, and insert the spike provided on the distal end of the IV line into a port on the intravenous fluid infusate bag or pouch. A fluid flow controller 30 allows infusate flow to be interrupted as necessary. In order to access a needleless connector port, the provider may remove a preinstalled disinfectant port cap by rotating the cap counterclockwise. Once the medication and/or fluid administration is complete, the provider may remove a replacement disinfection cap from a strip of replacement disinfection caps secured to the IV line and install the replacement cap on the needleless connector port by rotating the cap clockwise onto the port.

Referring to FIGS. 1-5, FIG. 1 illustrates use of an embodiment of the inventive kit once it is removed from the sterile packaging 34, shown in FIG. 1A. One end of the intravenous line may be secured to an IV fluid solution bag. The opposing end of the intravenous line may be secured to an intravenous catheter inserted into the patient; the catheter and patient are not shown. Needleless access ports 22 are pre-capped with disinfection caps 10 which prevent loss of sterility prior to use.

Figure 2:
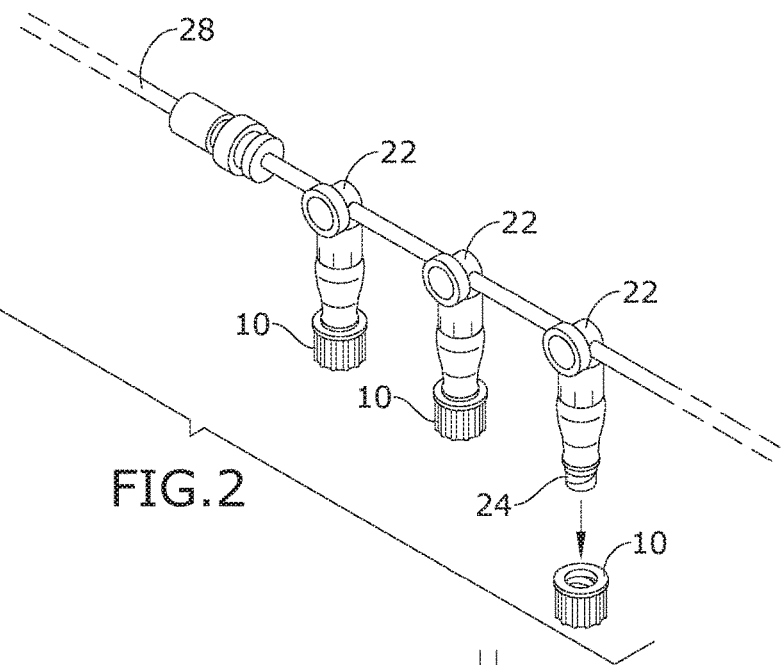
FIG. 2 is a detail view of the needleless ports of FIG. 1, showing removal of the cap.
Figure 3:
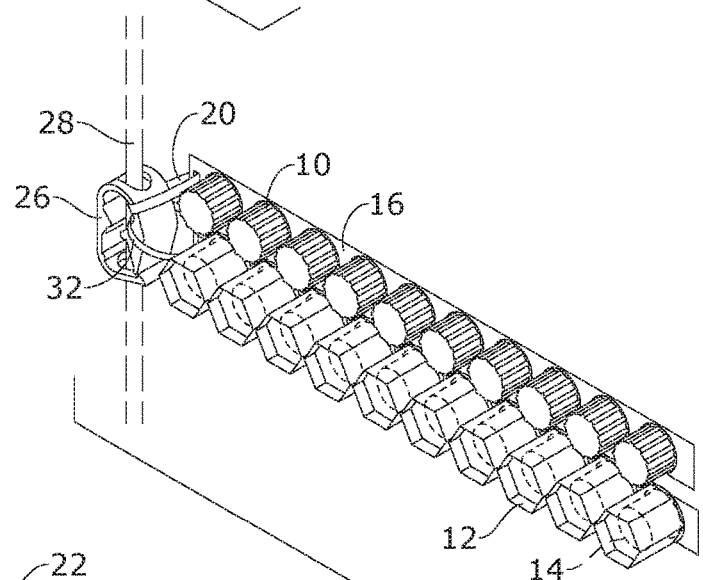
FIG. 3 is a detail view of replacement passive disinfection caps and the replacement active disinfection caps of FIG. 1.

As shown in FIG. 2, when access to a port 22 is required, for example to administer medication, disinfection cap 10 may be removed from the port 22 by twisting the cap 10 off a threaded connection 24 portion of the port. A strip 16 of passive disinfectant replacement caps 10 and a strip 18 of active disinfectant replacement caps 12 may be secured to the intravenous line 28 by way of a clip or clamp 26 and ties 20, 32, as shown in FIG. 3.

Figure 4:
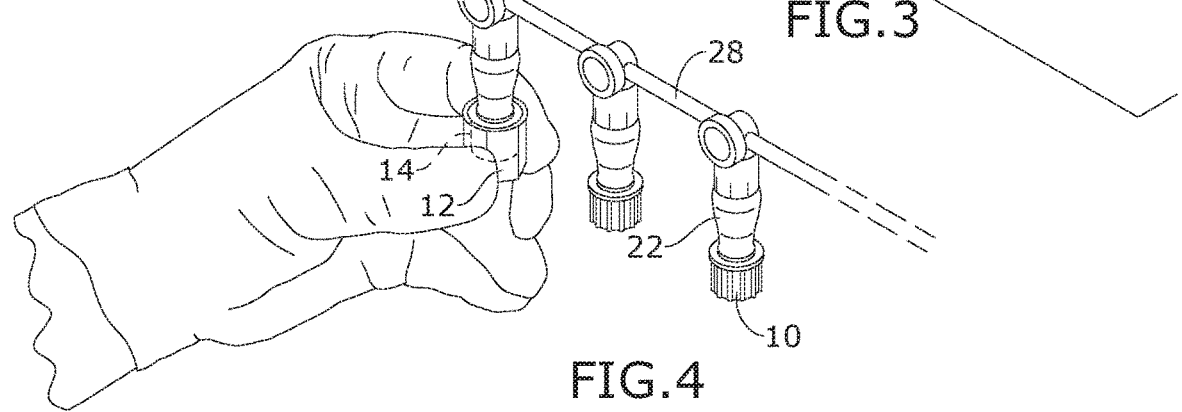
FIG. 4 is a detail perspective view of the embodiment of FIG. 1, showing use of a replacement active disinfection cap.

FIG. 4 illustrates use of an active disinfection cap 12, twisted onto the threaded connection 24 of access port 22, which further cleans the access port by abrasion from the textured interior surface 14.

Figure 5:
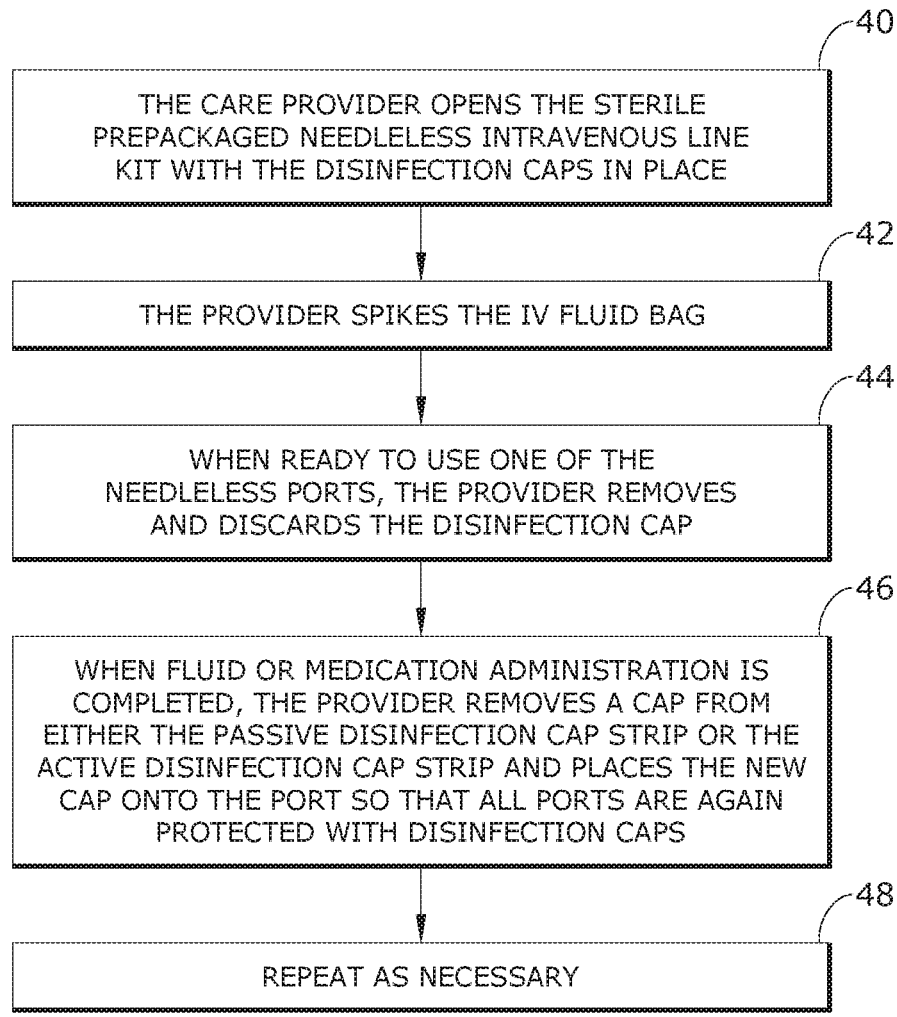
FIG. 5 is a flow chart of an embodiment of the invention.

FIG. 5 provides a flowchart of an embodiment of a method according to the invention. As shown, a method of keeping access ports 22 sterile to prevent nosocomial infections begins with opening the packaged intravenous line kit with pre-capped access ports 22. The provider may install the kit between the patient's catheter and the fluid infusion bag. In order to administer medication or other fluids, the provider may twist off the cap 10 to expose the access port 22. The removed cap 10 may be discarded. Once the provider finishes administering a substance to the IV line, a replacement cap 10, 12, may be twisted onto the access port 22 to disinfect the port 22 between uses. Each time a provider administers a substance, the steps of twisting of the disinfection cap and twisting on a replacement cap may be repeated.

It should be understood, of course, that the foregoing relates to exemplary embodiments of the invention and that modifications may be made without departing from the spirit and scope of the invention as set forth in the following claims.

What is claimed is:

1. A prepackaged needleless intravenous line assembly comprising:
   a. a pouch;
   b. a sterile intravenous line with at least one sterile access port sealed within the pouch; and
   c. at least one strip of a plurality of sealed disinfection caps sealed within the pouch;
   wherein the at least one sterile access port has a disinfection cap installed thereon; and
   wherein the plurality of sealed disinfection caps comprises a combination of passive disinfection caps and active disinfection caps.

2. The prepackaged needleless intravenous line assembly of claim 1, wherein the intravenous line is further provided with an infusion connector, for insertion into a pouch of intravenous fluid infusate, and a flow control device.

3. The prepackaged needleless intravenous line assembly of claim 1, wherein the disinfection caps are each impregnated with a disinfectant selected from the group consisting of alcohol and chlorhexidine.

4. The prepackaged needleless intravenous line assembly of claim 3, wherein at least one of the disinfection caps is impregnated with alcohol.

5. The prepackaged needleless intravenous line assembly of claim 1, wherein the plurality of sealed disinfection caps is attached to the intravenous tubing with a connector.

6. A method of delivering intravenous medication and/or fluid to a patient while maintaining sterility of a needleless access port, comprising:
   a. providing a pre-packaged intravenous tubing kit having
      i. sterile intravenous tubing with one or more sterile access ports, each access port having a disinfection cap installed thereon and
      ii. a plurality of sealed replacement disinfection caps;
   b. removing the intravenous tubing kit from the package and installing the tubing kit into an intravenous catheter placed in a patient;
   c. removing said disinfection cap from said sterile access port by twisting the disinfection cap to decouple threads;
   d. administering medication and/or fluid into said access port; and
   e. installing one of the plurality of replacement disinfection caps onto said access port by twisting the one of the plurality of replacement disinfection caps to couple threads, wherein the replacement disinfection caps are secured to the intravenous tubing by a connector, wherein the connector is selected from the group consisting of a zip tie; a pinch clamp; and a combination thereof.

7. The method of delivering intravenous medication and/or fluid to a patient while maintaining sterility of a needleless access port of claim 6, wherein an infusion connector is provided on a distal end of the intravenous tubing from the intravenous catheter, and wherein the method further comprises connecting the infusion connector to a pouch of intravenous fluid infusate.

8. The method of delivering intravenous medication and/or fluid to a patient while maintaining sterility of a needleless access port of claim 6, wherein the disinfection cap and the replacement disinfection caps are each selected from the group consisting of passive disinfection caps and active disinfection caps.

9. A replacement disinfection cap assembly, comprising:
a. a connector that is removably connectable to intravenous tubing; and
b. at least one strip with a plurality of disinfection caps connected to the connector;
   wherein the plurality of disinfection caps is selected from the group consisting of passive disinfection caps, active disinfection caps, and a combination thereof; and
   wherein the connector is selected from the group consisting of a zip tie; a pinch clamp; and a combination thereof.

10. The replacement disinfection cap assembly of claim 9, wherein the connector comprises a zip tie.

11. The replacement disinfection cap assembly of claim 9, wherein the connector comprises a pinch clamp.

12. The replacement disinfection cap assembly of claim 9, wherein the connector comprises a zip tie and a pinch clamp.

\* \* \* \* \*